(12) United States Patent
Perez et al.

(10) Patent No.: US 11,195,665 B2
(45) Date of Patent: Dec. 7, 2021

(54) TITANIUM CLAD NICKEL TERMINATION-PAD WELDED TO A TITANIUM TAB FOR A CAPACITOR

(71) Applicant: Greatbatch Ltd., Clarence, NY (US)

(72) Inventors: Anthony C. Perez, Wheatfield, NY (US); Kenneth B. Talamine, Plymouth, MN (US); Jason T. Hahl, East Aurora, NY (US)

(73) Assignee: Greatbatch Ltd., Clarence, NY (US)

( * ) Notice: Subject to any disclaimer, the term of this patent is extended or adjusted under 35 U.S.C. 154(b) by 234 days.

(21) Appl. No.: 16/291,061

(22) Filed: Mar. 4, 2019

(65) Prior Publication Data

US 2019/0272959 A1 Sep. 5, 2019

Related U.S. Application Data

(60) Provisional application No. 62/637,777, filed on Mar. 2, 2018.

(51) Int. Cl.

| H01G 9/06 | (2006.01) |
|---|---|
| H01G 9/10 | (2006.01) |
| H01G 9/008 | (2006.01) |
| H01G 9/08 | (2006.01) |
| H01G 9/145 | (2006.01) |
| H01G 9/02 | (2006.01) |
| H01G 9/052 | (2006.01) |
| A61N 1/39 | (2006.01) |

(52) U.S. Cl.
CPC .............. *H01G 9/06* (2013.01); *H01G 9/008* (2013.01); *H01G 9/08* (2013.01); *H01G 9/10* (2013.01); *H01G 9/145* (2013.01); *A61N 1/3956* (2013.01); *H01G 9/02* (2013.01); *H01G 9/052* (2013.01)

(58) Field of Classification Search
CPC .. H01G 9/10; H01G 9/06; H01G 9/08; H01G 9/008; H01G 9/0425; H01G 11/52; H01G 9/02; H01G 9/04; H01G 9/14; H01G 9/26; H01G 9/012; H01G 9/042; H01G 11/30; H01G 2009/05; Y02E 60/13
See application file for complete search history.

(56) References Cited

U.S. PATENT DOCUMENTS

| 5,894,403 | A | 4/1999 | Shah et al. |
|---|---|---|---|
| 5,920,455 | A | 7/1999 | Shah et al. |
| 6,224,985 | B1 | 5/2001 | Shah et al. |
| 6,468,605 | B2 | 10/2002 | Shah et al. |
| 7,012,799 | B2 | 3/2006 | Muffoletto et al. |
| 7,092,242 | B1 | 8/2006 | Gloss et al. |
| 7,271,994 | B2 | 9/2007 | Stemen et al. |
| 9,721,730 | B1 | 8/2017 | Muffoletto et al. |
| 9,824,829 | B1 | 11/2017 | Muffoletto et al. |

(Continued)

OTHER PUBLICATIONS

Extended European Search Report, Application 19160644.1, dated Jul. 5, 2019.

*Primary Examiner* — Imran Akram
(74) *Attorney, Agent, or Firm* — Michael F. Scalise

(57) ABSTRACT

A nickel termination-pad that has been clad-bonded to a titanium base layer electrically contacted to a casing to thereby serve as a surface for a device manufacturer to connect electronic circuit to the capacitor is described. The clad connection of the nickel termination-pad to the titanium base layer is both robust and provides good electrical conductivity between the dissimilar metals.

21 Claims, 9 Drawing Sheets

(56) References Cited

U.S. PATENT DOCUMENTS

| | | |
|---|---|---|
| 9,875,855 B2 | 1/2018 | Perez et al. |
| 9,978,528 B2 | 5/2018 | Hahl et al. |
| 10,020,127 B1 | 7/2018 | Muffoletto |
| 2005/0162810 A1 | 7/2005 | Seitz et al. |
| 2010/0134955 A1* | 6/2010 | O'Connor .............. H01G 11/54 |
| | | 361/508 |
| 2010/0187206 A1 | 7/2010 | Zhao et al. |
| 2012/0257327 A1 | 10/2012 | Zednickova et al. |

* cited by examiner

TITANIUM CLAD NICKEL TERMINATION-PAD WELDED TO A TITANIUM TAB FOR A CAPACITOR

CROSS-REFERENCE TO RELATED APPLICATION

The present application claims priority to U.S. provisional application Ser. No. 62/637,777, filed on Mar. 2, 2018.

BACKGROUND OF THE INVENTION

1. Field of the Invention

The present invention relates to capacitors, and more particularly to an improved termination-pad serving as an external connection to a capacitor.

2. Prior Art

Capacitors of the type that are used to power implantable medical device such as cardiac defibrillators are typically housed in casings formed of titanium. Device manufacturers generally prefer to connect a capacitor to circuits inside the medical device using a nickel termination-pad that in turn is electrically connected to the titanium casing. However, nickel does not readily connect to titanium, even when using a laser weld. It is not uncommon for intermetallics to form at the interface of the two metals, and intermetallics are characterized by brittleness, which is undesirable when a strong and robust weld is needed.

Therefore, there is a need to provide a nickel termination-pad for connecting an implantable capacitor to the device electronics as desired by medical device manufacturers while retaining titanium as a preferred casing material. An improved connection between the titanium casing and the nickel termination-pad is needed.

SUMMARY OF THE INVENTION

The present invention provides a nickel termination-pad that is clad-bonded to a titanium base layer. The clad connection of the nickel termination-pad to the titanium base layer is both robust and provides good electrical conductivity between the dissimilar metals. According to the present invention, a titanium casing tab for a cathode lead assembly is welded to the titanium casing and the titanium base layer of the termination-pad is welded to the casing tab. That way, the weld connections for the present capacitor are between similar metals. This helps ensure that the welds maintain their structural integrity and electrically conductivity for extended periods of time as needed in implantable medical devices.

These and other aspects of the present invention will become more apparent to those skilled in the art by reference to the following detailed description and to the appended drawings.

DETAILED DESCRIPTION OF THE PREFERRED EMBODIMENTS

Figure 1:
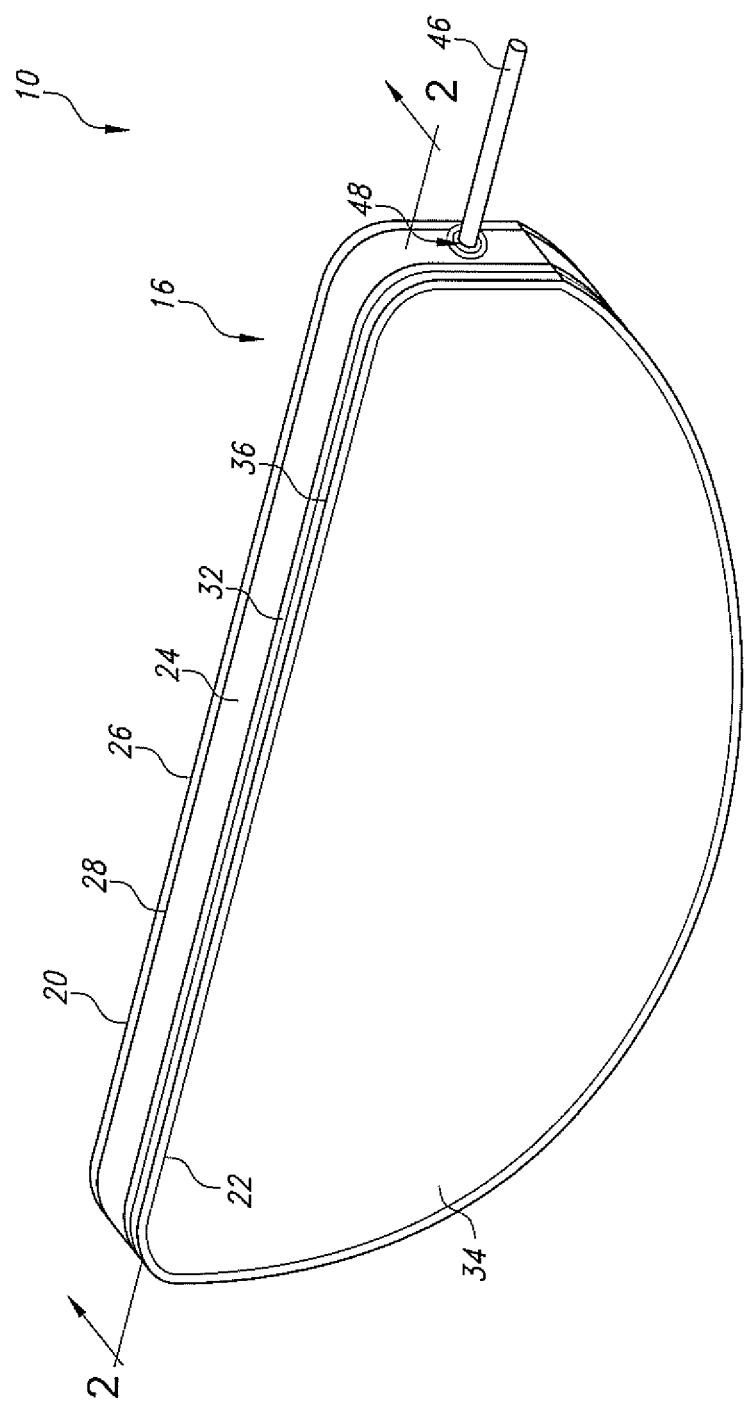
FIG. 1 is a perspective view of a capacitor 10 according to the present invention, but without the cathode terminal assembly shown in FIGS. 6A to 6C and the anode termination-pad 72 shown in FIGS. 7A to 7D.
Figure 2:
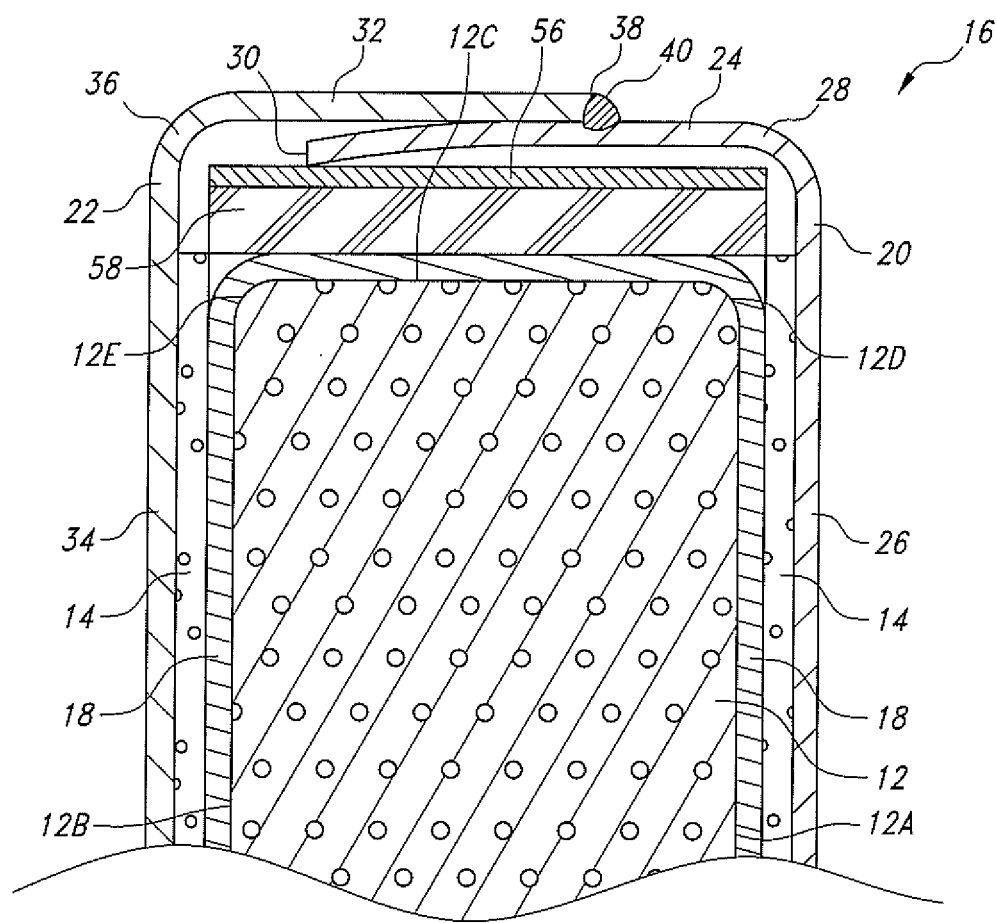
FIG. 2 is a partial cross-sectional view taken along line 2-2 of the capacitor 10 illustrated in FIG. 2.
Figure 3:
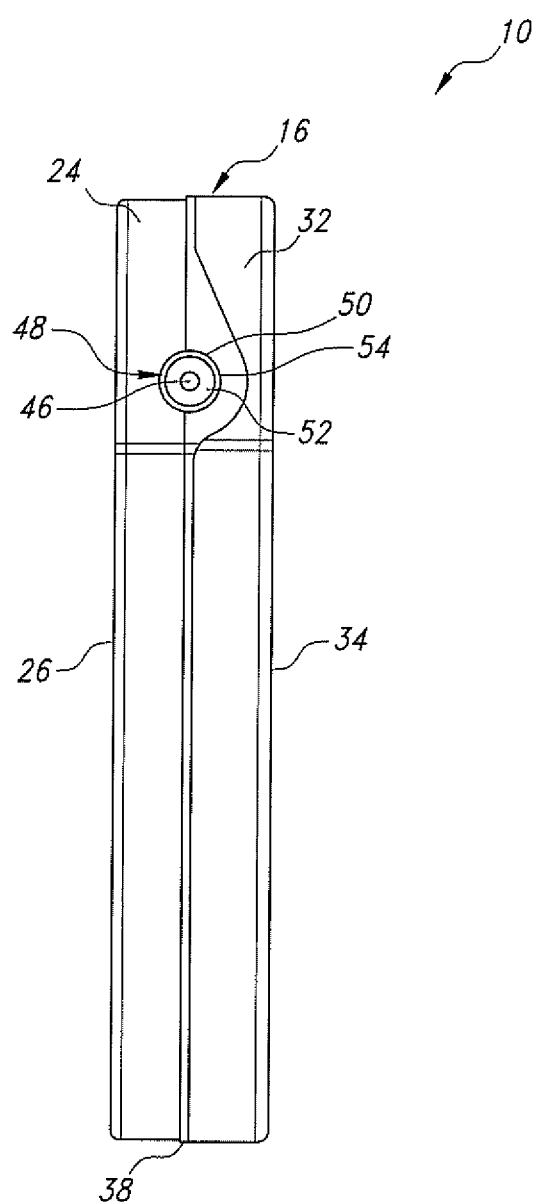
FIG. 3 is an elevational end view of the capacitor 10 shown in FIG. 1.

Referring now to the drawings, FIGS. 1 to 3 show an exemplary capacitor 10 according to the present invention. The capacitor 10 comprises an anode 12 of an anode active material and a cathode 14 of a cathode active material housed inside a hermetically sealed casing 16. The capacitor electrodes are prevented from direct physical contact with each other by a separator 18 that envelopes the anode 12. A working electrolyte (not shown) contained inside the casing 16 contacts the anode 12 and cathode 14. The capacitor 10 is of an electrolytic type with the cathode 14 comprising a conductive material having capacitive properties.

The casing 16 is of a metal material comprising first and second drawn clamshell-type casing portions 20 and 22. The casing portions 20, 22 are preferably selected from the group consisting of titanium, tantalum, nickel, molybdenum, niobium, cobalt, stainless steel, tungsten, platinum, palladium, silver, copper, chromium, vanadium, aluminum, zirconium, hafnium, zinc, iron, and mixtures and alloys thereof. In addition to being of a drawn form, the clamshell-type casing portions 20, 22 can be of a machined construction or be formed by a metal injection molding process. Preferably, the casing portions have a thickness of about 0.001 inches to about 0.015 inches.

The first clamshell-type casing portion 20 comprises a surrounding sidewall 24 extending to and meeting with a major face wall 26 at a curved intermediate bend 28. Opposite bend 28, the surrounding sidewall 24 extends to a continuous, perimeter edge 30. Similarly, the second clamshell-type casing portion 22 comprises a surrounding sidewall 32 extending to and meeting with a major face wall 34 at a curved intermediate bend 36. Opposite bend 36, the surrounding sidewall 32 extends to a continuous perimeter edge 38. However, face wall 26 is somewhat smaller than face wall 34 so that its surrounding sidewall 24 fits inside the surrounding sidewall 32 of the second casing portion 22 in an overlapping, contact relationship. That way, casing 16 is hermetically sealed by providing a weld 40 at the surrounding sidewall 24 of the first casing portion 20 and the edge 38 of the second casing portion 22.

Other casing structures that are useful with the present invention are described in U.S. Pat. No. 7,012,799 to Muffoletto et al., U.S. Pat. No. 7,092,242 to Gloss et al., U.S. Pat. No. 7,271,994 to Stemen et al., U.S. Pat. No. 9,978,528 to Hahl et al., U.S. Pat. No. 9,721,730 to Muffoletto et al., U.S. Pat. No. 9,824,829 to Muffoletto et al., U.S. Pat. No. 9,875,855 to Perez et al. and U.S. Pat. No. 10,020,127 to Muffoletto, all of which are assigned to the assignee of the present invention and incorporated herein by reference.

The anode 12 is of an active metal that is typically selected from the group consisting of tantalum, aluminum, titanium, niobium, zirconium, hafnium, tungsten, molybdenum, vanadium, silicon, germanium, and mixtures thereof. As is well known by those skilled in the art, the anode metal in powdered form, for example tantalum powder, is compressed into a pellet of a desired shape. In the illustrated embodiment, the anode pellet is of a substantially uniform thickness between spaced apart right and left major sidewalls 12A, 12B joined by an end wall 12C. The major sidewalls 12A, 12B meet the intermediate wall 12C at respective curved edges 12D, 12E. The curved edges 12D, 12E are of a substantially similar radius as that of the casing bends 28, 36, respectively.

The cathode active material 14 preferably coats the inner surfaces of the major face walls 26, 34 of the respective casing portions 20, 22 in a pattern that generally mirrors the shape of the right and left major sidewalls 12A, 12B of the anode 12. The cathode active material 14 preferably has a thickness of about a few hundred Angstroms to about 0.1 millimeters and is either directly coated on the inner surfaces of the face walls 26, 34 or it is coated on a conductive substrate (not shown) supported on and in electrical contact with the inner surfaces thereof. The cathode material coatings are preferably spaced from the surrounding sidewalls 24, 32 of the respective casing portions 20, 22.

In that respect, the major face walls 26, 34 of the casing portions 20, 22 may be of an anodized-etched conductive material, have a sintered active material with or without oxide contacted thereto, be contacted with a double layer capacitive material, for example a finely divided carbonaceous material such as graphite, carbon, platinum black, a redox, pseudocapacitive, or an under potential material, or be an electroactive conducting polymer such as polyaniline, polypyrrole, polythiophene, polyacetylene, and mixtures thereof.

According to one preferred aspect of the present invention, the redox or cathode active material 14 includes an oxide of a metal, a nitride of the metal, a carbon nitride of the metal, and/or a carbide of the metal, the oxide, nitride, carbon nitride and carbide having pseudocapacitive properties. The metal is preferably selected from the group consisting of ruthenium, cobalt, manganese, molybdenum, tungsten, tantalum, iron, niobium, iridium, titanium, zirconium, hafnium, rhodium, vanadium, osmium, palladium, platinum, nickel, and lead. In a preferred embodiment of the present invention, the cathode active material 14 includes an oxide of ruthenium or oxides of ruthenium and tantalum.

A pad printing process as described in U.S. Pat. No. 7,116,547 to Seitz et al. is preferred for providing such a coating. An ultrasonically generated aerosol as described in U.S. Pat. Nos. 5,894,403, 5,920,455, 6,224,985, and 6,468,605, all to Shah et al., is also a suitable deposition method. These patents are assigned to the assignee of the present invention and incorporated herein by reference.

Figure 4:
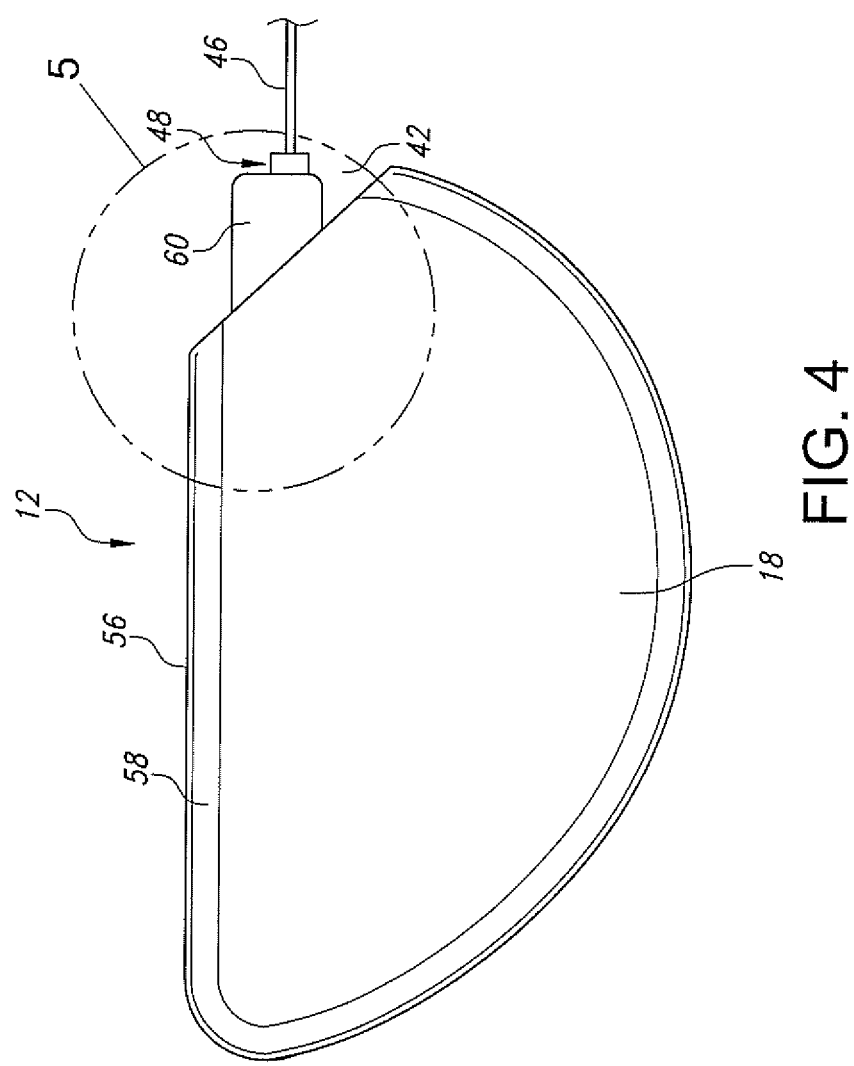
FIG. 4 is a side elevational view of the anode 12 for capacitor 10 with the anode including an anode lead 46 extending through a glass-to-metal-seal 48.
Figure 5:
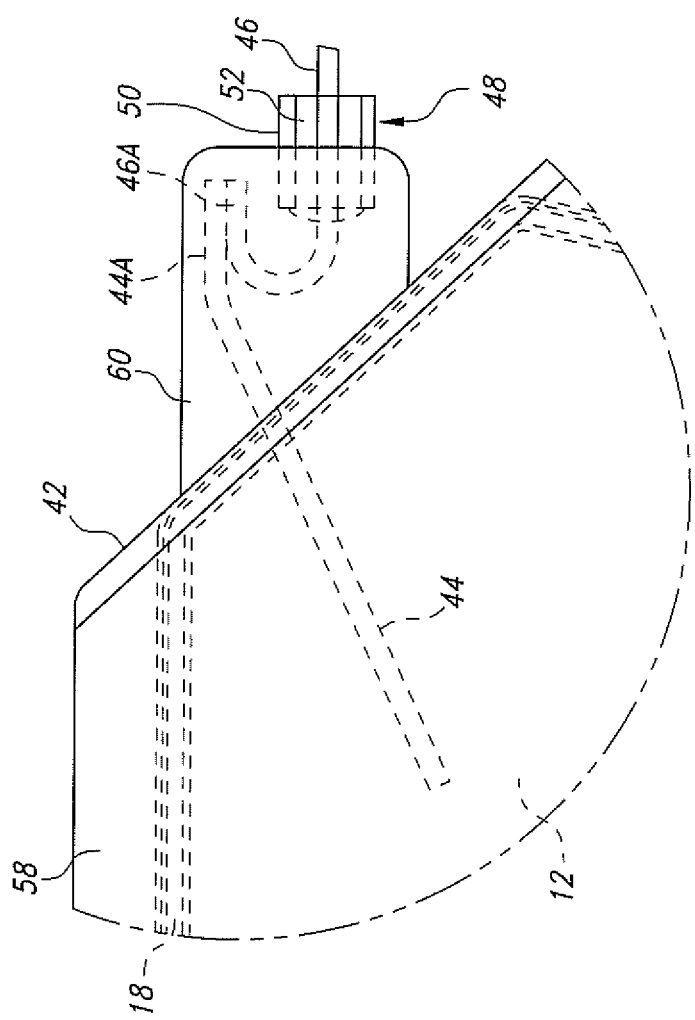
FIG. 5 is an enlarged view of the portion indicated in FIG. 4 showing an embedded anode wire 44 extending outwardly from the anode 12 and being connected to the anode lead 46 extending through the glass-to-metal-seal 48.

As shown in FIGS. 4 and 5, the anode 12 further comprises a notch 42 from which an embedded anode wire 44 extends. The anode wire 44 is preferably of the same material as the anode active material. The anode pellet is sintered under a vacuum at high temperatures and then anodized in a suitable electrolyte. The anodizing electrolyte fills the pores of the pressed powder body and a continuous dielectric oxide is formed thereon. In that manner, the anode 12 and extending wire 44 are provided with a dielectric oxide layer that is formed to a desired working voltage.

After the anode 12 and extending wire 44 are anodized to the desired formation voltage, the anode wire 44 is subsequently connected to an anode lead 46 supported in an insulative glass-to-metal seal 48 (GTMS). The glass-to-metal seal 48 comprises a ferrule 50 defining an internal cylindrical through bore or passage of constant inside diameter. An insulative glass 52 provides a hermetic seal between the ferrule bore and the anode lead 46 passing there through. The glass 52 is, for example, ELAN® type 88 or MANSOL™ type 88. Anode lead 46 has a J-shaped proximal portion 46A that is connected to a distal portion 44A of the anode wire 44. Laser welding secures the distal portion 44A of the anode wire 44 to the J-shaped proximal portion 46A of the anode lead 46.

The separator 18 (FIG. 2) is of electrically insulative material in the shape of a bag that, except for the extending anode wire 44, surrounds and envelops the anode 12. The separator 18 prevents an internal electrical short circuit between the anode 12 and cathode active materials 14 in the assembled capacitor and has a degree of porosity sufficient to allow flow there through of the working electrolyte during the electrochemical reaction of the capacitor 10. Illustrative separator materials include woven and non-woven fabrics of polyolefinic fibers including polypropylene and polyethylene or fluoropolymeric fibers including polyvinylidene fluoride, polytetrafluoroethylene, and polyethylenechlorotrifluoroethylene laminated or superposed with a polyolefinic or fluoropolymeric microporous film, non-woven glass, glass fiber materials and ceramic materials. Additional separator materials may include films of poly sulfone and polyester, for example, polyethylene terephthalate. Suitable microporous films include a polyethylene membrane commercially available under the designation SOLUPOR® (DMS Solutech), a polytetrafluoroethylene membrane commercially available under the designation ZITEX® (Chemplast Inc.) or EXCELLEPATOR® (W. L. Gore and Associates), a polypropylene membrane commercially available under the designation CELGARD® (Celanese Plastic Company, Inc.), and a membrane commercially available under the designation DEXIGLAS® (C. H. Dexter, Div., Dexter Corp.). Cellulose based separators are also useful. Depending on the electrolyte used, the separator 18 can be treated to improve its wettability, as is well known by those skilled in the art.

A preferred separator 18 comprises a non-woven layer of polyethylene or polypropylene, a microporous layer of polyethylene or polypropylene, and, possibly a third layer of polyethylene or polypropylene, which is also non-woven. The preferred separator 18 has a melting temperature of about 140° C. and must be protected from the heat generated when the edge 38 of casing portion 22 is secured to the surrounding sidewall 24 of casing portion 20 by weld 40. The other separator materials described above likewise have relatively low melting temperatures in comparison to the heat generated by the welding operation used to secure the casing portions 20, 22 together. This is even when the temperature is measured at the separator portion covering the anode end wall 12C.

After the cathode active material 14 is contacted to the inner surfaces of the major face walls 26, 34 of the clamshell-type casing portions 20, 22, the anode 12 enveloped in the separator 18 is nested in the smaller casing portion 20 with a distal step of the GTMS 48 received in an opening 54 (FIG. 3) in the casing sidewall 24 in a tight-fitting relationship. The ferrule 50 is then secured to the surrounding sidewall 24 by a laser weld. In the final capacitor assembly, the GTMS 48 electrically insulates the anode lead 46 electrically connected to the anode wire 44 from the metal casing 16. In that manner, the anode lead 46 extending from inside the casing to outside thereof and being electrically insulated from the casing 16 by the GTMS 48 serves as the positive terminal for the capacitor 10.

As shown in FIG. 2, a weld strap 56 is provided directly adjacent to the surrounding sidewall 24 of casing portion 20. The weld strap 56 is an annular, ring-shaped member surrounding the anode end wall 12C and is typically of the same metal as that of the casing portions 20, 22. An intermediate polymeric insulating ring 58 seats against the weld strap 56 and the separator 18 portion covering the anode end wall 12C. The weld strap 56 in conjunction with the insulating ring 58 help shield the separator 18 at the anode end wall 12C from the heat generated as the casing portions 20, 22 are welded together. A polymeric material 60 encases the GTMS 48 including the anode wire 44 connected to the anode lead 46. This helps stabilize these components from movement should the capacitor be subjected to rough handling, and the like.

A working electrolyte (not shown) is then provided in the capacitor through an opening in one of the casing portions 20, 22. The working electrolyte thoroughly wets the anode 12 including the enveloping separator 18 and the cathode active materials 14 to provide the capacitor 10 in a functional state. A suitable working electrolyte for the capacitor 10 is described in U.S. Pat. No. 6,219,222 to Shah et al., which includes a mixed solvent of water and ethylene glycol having an ammonium salt dissolved therein. U.S. Pub. No. 2003/0090857 and U.S. Pat. No. 6,687,117, both to Liu et al., describe other working electrolytes that are suitable for use with the present capacitors. The working electrolyte of the former publication comprises water, a water-soluble inorganic and/or organic acid and/or salt, and a water-soluble nitro-aromatic compound while the latter publication relates to a working electrolyte comprising de-ionized water, an organic solvent, isobutyric acid and a concentrated ammonium salt. The '222 patent, the '857 publication and the '117 patent are assigned to the assignee of the present invention and incorporated herein by reference. A closure member (not shown) is hermetically welded in the electrolyte fill opening to seal the casing 16.

Figure 6A:
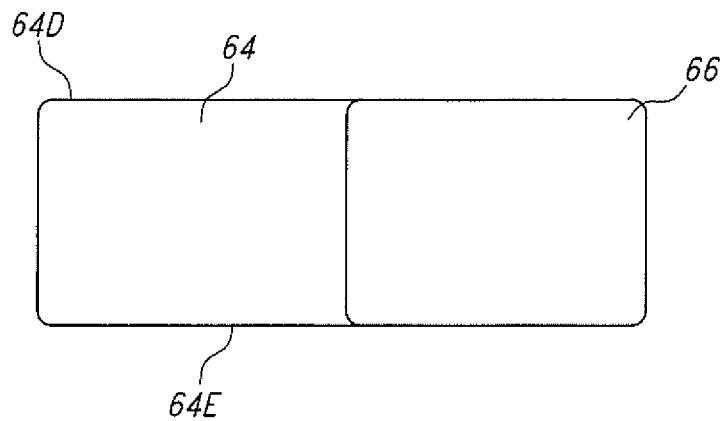
FIG. 6A is a plan view of a cathode terminal pad assembly 62 according to the present invention.
Figure 6B:
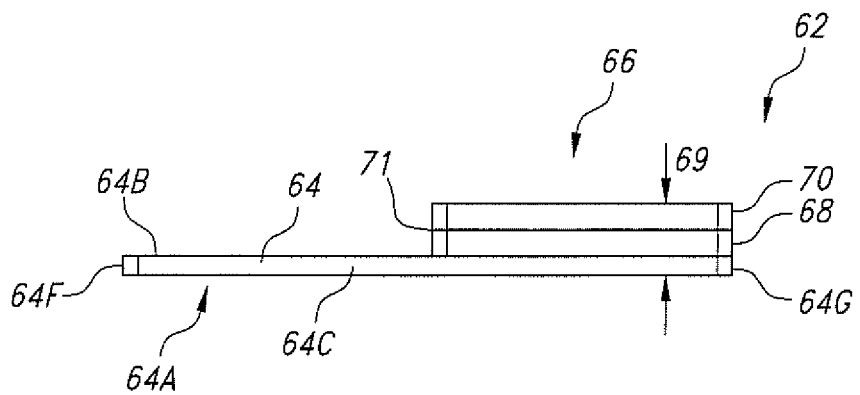
FIG. 6B is a side elevation view of the cathode terminal pad assembly 62 shown in FIG. 6A.
Figure 6C:
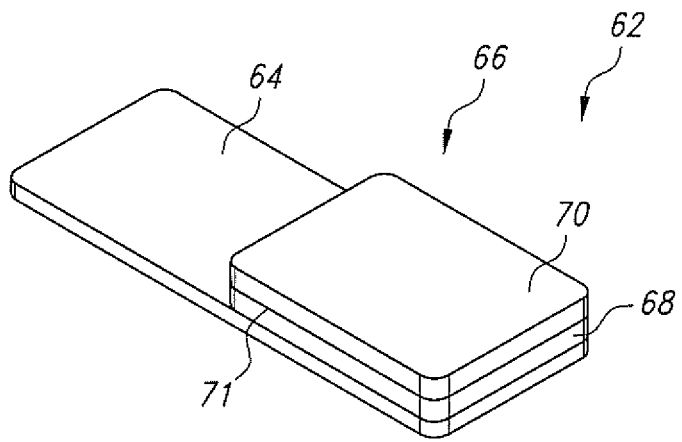
FIG. 6C is a perspective view of the cathode terminal pad assembly 62 shown in FIGS. 6A and 6B.

The casing 16 comprising the mating clamshell-type portions 20, 22 being of a conductive metal serves as the cathode or negative terminal for the capacitor 10. FIGS. 6A to 6C illustrate a cathode terminal assembly 62 that is electrically supported by the casing 16 as a convenient structure for connecting to the negative terminal. The cathode terminal assembly 62 comprises a casing tab 64 supporting a termination-pad subassembly 66. The casing tab 64 has a lower surface 64A which contacts the casing 16 and is spaced from an upper surface 64B by an intermediate edge 64C. The casing tab 64 is a generally rectangular-shaped member defined by opposed first and second long sides 64D and 64E extending to and meeting with third and fourth relatively shorth sides 64F and 64G. The long sides 64D, 64E and shorth sides 64F, 64G meet at included curved edges.

It is within the scope of the present invention that the cathode tab 64 need not be rectangular but can have a myriad of different shapes dictated by the form factor of the capacitor on which it is to be mounted. Preferably, the long sides 64D, 64E of the casing tab align with the length of the overlapping surrounding edges 24, 32 of the clamshell-type casing portions 20, 22. This orientation provides the capacitor 10 with a relatively thin form factor suitable for powering an implantable medical device, such as a cardiac defibrillator.

Casing tab 64 supports the termination-pad subassembly 66 spaced from the casing 16. The termination-pad subassembly 66 is of a clad construction comprising a base layer 68 that is clad-bonded to a termination-pad layer 70 at a bond interface 71. While the various figures show the base layer 68 contacting the termination-pad layer 70 at a lower surface thereof spaced from an upper surface where the device manufacturer will later connect circuits to the termination-pad layer, it is within the scope of the present invention that the base layer can also be clad-bonded along the edge of the termination-pad layer 70. All that is needed is that the upper surface of the termination-pad layer 70 remain unobstructed for ease of later connection to the device circuits.

Cladding is defined as the bonding together of dissimilar metals, and is often achieved by extruding two metals through a die or by pressing or rolling sheets of dissimilar metals together under high pressure. Suitable cladding techniques include roll bonding, explosive welding, and laser cladding.

In roll bonding, layers of different metals, for example titanium and nickel, are cleaned and passed through a pair of rollers under sufficient pressure to bond the layers. The pressure is high enough to deform the metals and reduce the combined thickness of the clad materials. If desired, heat may be applied.

In explosive welding, bond pressure is provided by detonation of a sheet of chemical explosive and no heat-affected zone is produced in the bond between the metals.

Laser cladding is a method where a powdered or wire feedstock of nickel is melted and consolidated by use of a laser to coat the lower surface of the base layer 68.

The base layer 68 termination-pad subassembly 66 is desirably of the same material as the casing tab 64 which in turn is of the same material as the casing portions 20, 22. Titanium is a commonly used material for the casing portions 20, 22 as it is well known for its biocompatibility and as a material that can be formed such as by drawing, and the like, into shapes that are typical for capacitors that are intended to power implantable medical devices. However, it is within the scope of the present invention that the casing tab 64 and base layer 68 can be constructed of any of the previously enumerated materials that are suitable for the casing portions 20, 22.

In that respect, when the casing portions 20, 22 are of titanium, it is desirable for the casing tab 64 and the base layer 68 to also be of titanium. However, device manufactures typically prefer nickel as a bond-pad or termination-pad material to which they will electrically connect circuits inside the medical device that the capacitor is intended to power. It is recognized that welding a nickel termination-pad to a titanium casing tab can create a weld that is brittle and susceptible to cracking due to the morphology of the dissimilar metals. The present invention improves this connection structure by clad-bonding the titanium base layer 68 to the nickel termination-pad layer 70 of the termination-pad subassembly 66. This termination-pad subassembly 66 is then readily connectible to the titanium casing tab 64 by various welding techniques. One preferred method is by resistance welding. As indicated by arrows 69 in FIG. 6B, resistance welding is from the casing tab 64 and the termination-pad layer 70 toward the intermediate base layer 68.

Figure 8:
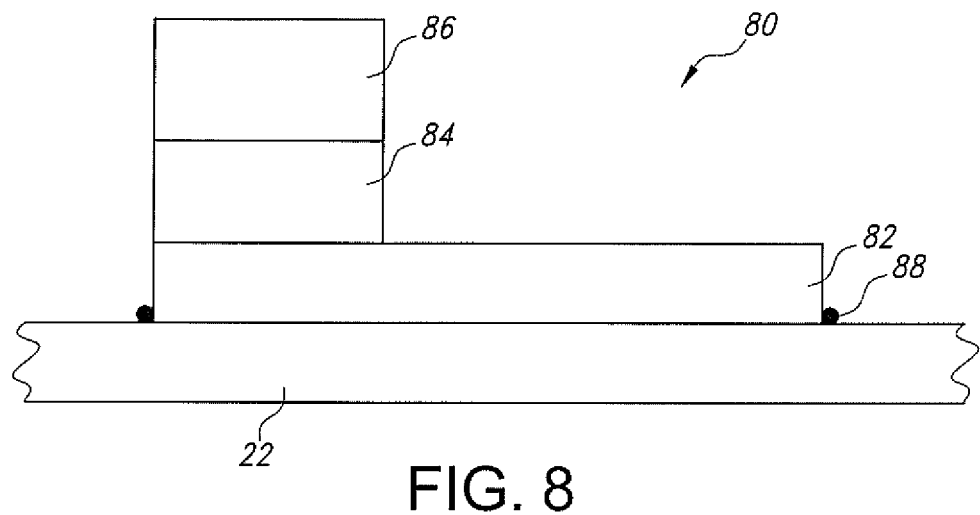
FIG. 8 is a side elevational view of an alternate embodiment of a cathode terminal assembly 80 according to the present invention.

FIG. 8 illustrates an alternate embodiment for a cathode terminal assembly 80 according to the present invention. In a similar manner as with the previously described cathode terminal assembly 62, assembly 80 comprises a titanium casing tab 82 supporting a titanium base layer 84 that is clad-bonded to a nickel termination-pad layer 86. Whereas the cathode terminal assembly 62 was resistance welded to the casing portion 22, cathode terminal assembly 80 has the base layer 84 electrically connected to the casing portion 22 by a weld 88, for example a laser weld. This construction provides a direct line-of-sight perspective for seeing the weld as it is being formed. The previously described resistance weld does not have this line-of-sight attribute.

Figure 7A:
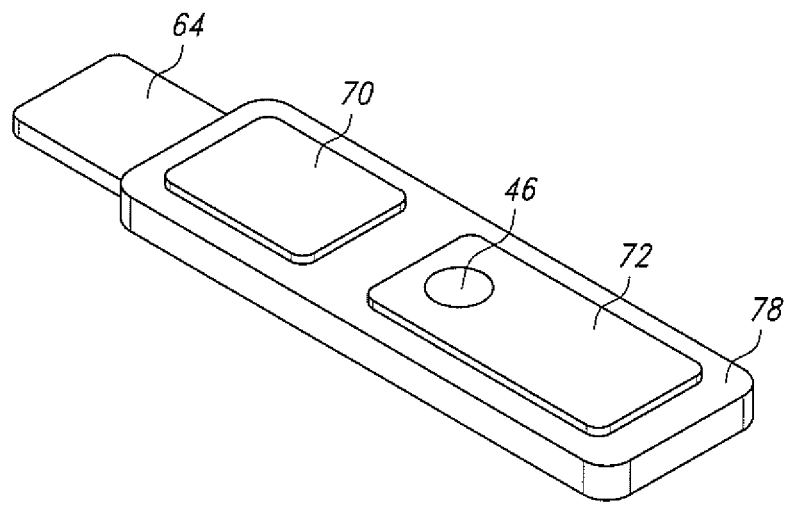
FIG. 7A is a perspective view of the cathode terminal pad assembly 62 shown in FIGS. 6A to 6C and an anode termination-pad 72 for the anode lead 46.
Figure 7B:
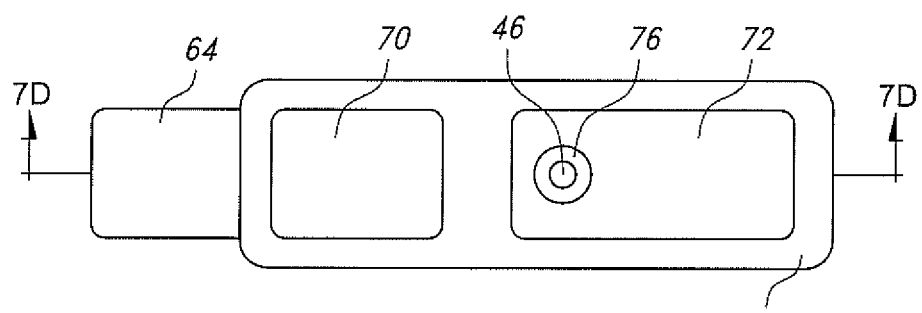
FIGS. 7B and 7C illustrate a plan view and a side elevational view, respectively, of the cathode terminal pad assembly 62 shown in FIGS. 6A to 6C and the anode termination-pad 72/anode lead 46 shown in FIG. 7A.
Figure 7C:
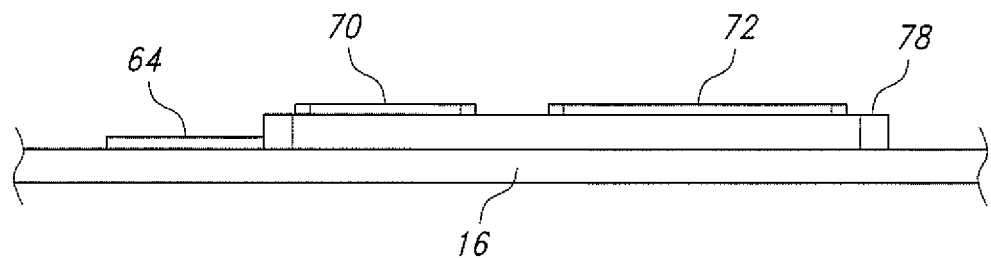
Figure 7D:
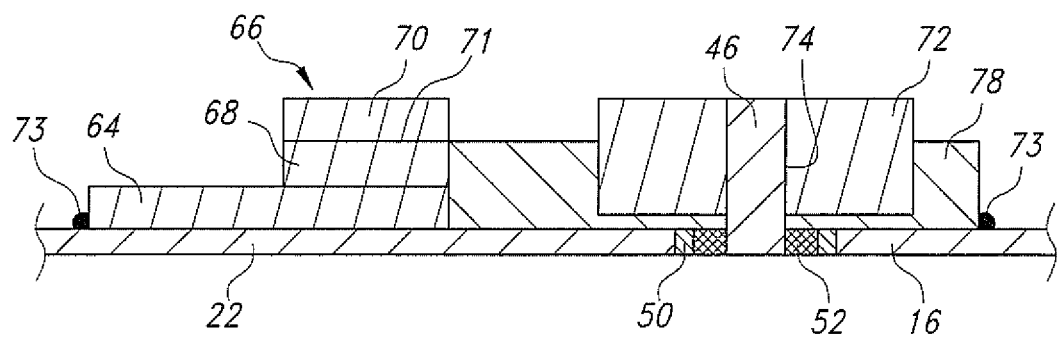
FIG. 7D is a cross-sectional view taken along line 7D-7D of FIG. 7A.

FIG. 7C illustrates the cathode terminal assembly 62 comprising the casing tab 64 mounted to the casing 16 in an electrically conductive connection and with the previously described titanium base layer 68 clad-bonded to the nickel termination-pad 70 being supported on the casing tab 64. The previously described anode lead 46 is provided with a anode termination-pad 72, which is preferably made of nickel. The anode termination-pad 72 is provided with an opening 74 that receives the anode lead 46. A weld 76 (FIG. 7B) connects the tantalum anode lead 46 to the nickel anode termination-pad 72. Since the casing 16 is of a negative polarity, the anode termination-pad 72 is spaced from the casing 16 by a suitable distance that ensures electrical isolation between the casing and the anode termination-pad.

Then, with the cathode terminal assembly 62 electrically connected to the casing 16 serving as the negative terminal and the anode termination-pad 72 connected to the anode lead 46 spaced from the casing serving as the positive terminal for the capacitor 10, this opposite polarity terminal assembly is partially encased in an insulating polymeric material 78. Polyoxymethylene (POM), also known as acetal, polyacetal, and polyformaldehyde, is a suitable polymeric material for this purpose.

Figure 9:
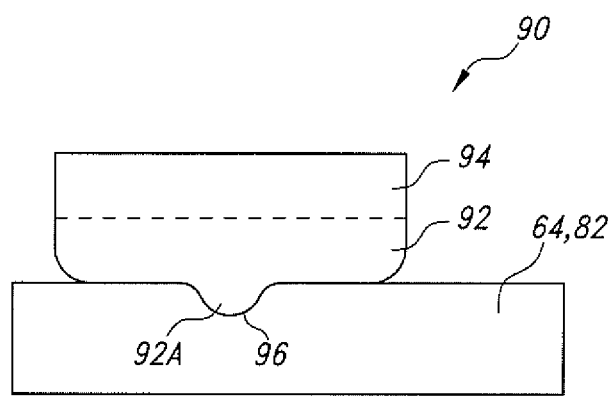
FIG. 9 is a side elevational view of an alternate embodiment of nickel clad termination-pad 90 according to the present invention.

FIG. 9 illustrates an alternate embodiment of a clad termination-pad subassembly 90 according to the present invention. Termination-pad subassembly 90 comprises a titanium base layer 92 that is clad bonded to a nickel termination-pad 94. However, the base layer 92 is provided with a curved protrusion 92A, preferably centered, that extends outwardly opposite the nickel termination-pad 94. The protrusion 92A is received in a mating indentation 96 in the casing tab 64, 82 of the respective cathode terminal assemblies 62, 80. This structure provides for centering the nickel clad termination-pad with the casing tab 64, 82.

Thus, various embodiments for providing a nickel termination-pad as a negative or cathode terminal for a capacitor are described. As an improvement over the convention method of welding a nickel termination-pad to a titanium casing tab, and the drawbacks inherent in fusing those dissimilar metals together, the present invention describes a nickel termination-pad that is clad-bonded to a titanium base layer. The clad connection is both robust and provides good electrical conductivity between the dissimilar metals. Otherwise, the weld connections for the cathode or negative terminal are between similar metals, which do not create undesirable intermetallics. That is, the titanium base layer of the termination-pad subassembly is welded to the titanium casing tab and the casing tab 64 is welded to the titanium casing.

It is appreciated that various modifications to the present inventive embodiments described herein may be apparent to those of ordinary skill in the art without departing from the scope of the present invention as defined by the herein appended claims.

What is claimed is:

1. A capacitor, which comprises:
    a) a casing comprising a first metal casing portion hermetically sealed to a second metal casing portion;
    b) a first electrode comprising a first electrode active material housed inside and in electrical contact with the casing;
    c) a first electrode terminal comprising a first electrode casing tab directly arid electrically contacted to an outer surface of the casing, and a first electrode nickel termination-pad electrically connected to the first electrode casing tab opposite the casing;
    d) a second electrode comprising a second electrode lead wire extending outwardly from a second electrode active material housed inside the casing, the second electrode active material being of an opposite polarity to that of the first electrode active material, wherein a glass-to-metal seal supports and electrically insulates the second electrode lead wire from the casing, and wherein an external portion of the second electrode lead wire residing outside the casing is electrically connected to a second electrode nickel termination-pad of an opposite polarity to that of the first electrode casing tab contacted to the first electrode nickel termination-pad, the second electrode nickel termination-pad being electrically insulated from the casing;
    e) a separator disposed between the first and second active materials to prevent them from directly contacting each other; and
    f) a working electrolyte provided in the casing in contact with the first and second electrode active materials.

2. The capacitor of claim 1, wherein the casing and the first electrode casing tab are both made of titanium.

3. The capacitor of claim 1, wherein a first electrode titanium base layer resides between and is directly and electrically contacted to the first electrode casing tab and the first electrode nickel termination-pad.

4. The capacitor of claim 3, wherein the first electrode nickel termination-pad is clad-bonded to the first electrode titanium base layer.

5. The capacitor of claim 3, wherein the first electrode titanium base layer has an outwardly extending curved protrusion that is received in a mating indentation in the first electrode casing tab contacted to the outer surface of the casing.

6. The capacitor of claim 1, wherein the casing comprises:
    a) a first metal casing member having a first surrounding side wall extending to and meeting with a first continuous major face wall; and
    b) a second metal casing member having a second surrounding side wall extending to and meeting with a second continuous major face wall, c) wherein the first and second casing members are mated to each other so that a first outer edge of the first surrounding side wall faces the second major face wall with at least a portion of the second surrounding side wall being in an overlapping, direct contact relationship with at least a portion of the first surrounding side wall to form a seam; and d) a weld hermetically sealing the first and second casing members together at the seam, thereby providing the casing housing the separator intermediate the first and second electrodes and the working electrolyte.

7. The capacitor of claim 1, wherein the first electrode active material is a cathode active material characterized as having been contacted to the casing by either a pad printing process or as an ultrasonically deposited spray.

8. The capacitor of claim 1, wherein:
a) the first electrode active material is a cathode active material that is selected from the group of ruthenium, cobalt, manganese, molybdenum, tungsten, tantalum, iron, niobium, iridium, titanium, zirconium, hafnium, rhodium, vanadium, osmium, palladium, platinum, nickel, lead, gold, silver, cobalt, and mixtures thereof, and b) the second electrode active material is an anode active material selected from the group of tantalum, aluminum, titanium, niobium, zirconium, hafnium, tungsten, molybdenum, vanadium, silicon, germanium, and mixtures thereof.

9. The capacitor of claim 1, wherein the first electrode active material is a cathode active material selected from the group of an anodized-etched foil, a sintered active material with or without oxide, a double layer capacitive material, a pseudocapacitive material, and a conductive polymeric material.

10. The capacitor of claim 9, wherein the pseudocapacitive material is selected from the group of ruthenium, molybdenum, tungsten, tantalum, cobalt, manganese, nickel, iridium, iron, titanium, zirconium, hafnium, rhodium, vanadium, osmium, palladium, platinum and niobium, and mixtures thereof.

11. The capacitor of claim 10, wherein the pseudocapacitive material is selected from the group of an oxide, a nitride, a carbon nitride and a carbide, and mixtures thereof.

12. The capacitor of claim 1, wherein the first electrode active material is comprised of ruthenium oxide and the second electrode active material is comprised of tantalum.

13. The capacitor of claim 1, wherein the second electrode nickel termination-pad is electrically insulated from the casing by an insulating polymeric material residing between the outer surface of the casing and the second electrode nickel termination-pad electrically connected to the external portion of the second electrode lead wire.

14. A capacitor, which comprises:
a) a casing comprising a first metal casing portion hermetically sealed to a second metal casing portion;
b) a cathode comprising a cathode active material housed inside and electrically contacted to the casing;
c) a cathode terminal comprising a cathode casing tab directly and electrically contacted to an outer surface of the casing and a cathode nickel termination-pad electrically connected to the cathode casing tab opposite the casing;
d) an anode comprising an anode lead wire extending outwardly from an anode active material housed insider the casing, wherein a glass-to-metal seal supports arid electrically insulates the anode lead wire from the casing, and wherein an external portion of the anode lead wire residing outside the casing is electrically connected to an anode nickel termination-pad, the anode nickel termination-pad being electrically insulated from the casing by an insulatin polymeric material;
e) a separator disposed between the cathode and anode active materials to prevent them from directly contacting each other; and
f) a working electrolyte provided in the casing in contact with the cathode and anode active materials.

15. The capacitor of claim 14, wherein the casing and the cathode casing tab are both made of titanium.

16. The capacitor of claim 14, wherein a titanium cathode base layer resides between and is directly and electrically contacted to the cathode casing tab and the cathode nickel termination-pad.

17. The capacitor of claim 16, wherein the cathode nickel termination-pad is clad-bonded to the cathode titanium base layer.

18. The capacitor of claim 14, wherein the cathode casing tab electrically connected to the cathode nickel termination-pad, and the anode nickel termination-pad electrically connected to the external portion of the anode lead wire, but electrically insulated from the casing, reside side-by-side outside the casing.

19. The capacitor of claim 14, wherein the insulating polymeric material contacts both the casing and the anode nickel termination-pad electrically connected to the external portion of the anode lead wire.

20. The capacitor of claim 14, wherein the insulating polymeric material residing between and in contact with the casing and the anode nickel termination-pad also contacts the cathode casing tab electrically connected to the cathode nickel to termination-pad.

21. A capacitor, which comprises:
a) a casing comprising a first titanium casing portion hermetically sealed to a second titanium casing portion;
b) a cathode comprising a ruthenium oxide cathode active material housed inside and electrically contacted to an inner surface of the casing;
c) a cathode terminal comprising a cathode titanium casing tab directly and electrically contacted to an outer surface of the casing, and a cathode nickel termination-pad electrically connected to the cathode titanium casing tab opposite the casing;
d) an anode comprising an anode lead wire extending outwardly from a tantalum anode active material housed inside the casing, wherein a glass-to-metal seal supports and electrically insulates the tantalum anode lead wire from the casing, and wherein an external portion of the tantalum anode lead wire residing outside the casing is electrically connected to an anode nickel termination-pad, the anode nickel termination pad being insulated from the casing;
e) a separator disposed between the ruthenium oxide and tantalum active materials to prevent them from directly contacting each other; and
f) a working electrolyte provided in the casing in contact with the ruthenium oxide and tantalum active materials.

* * * * *

UNITED STATES PATENT AND TRADEMARK OFFICE
CERTIFICATE OF CORRECTION

PATENT NO. : 11,195,665 B2
APPLICATION NO. : 16/291061
DATED : December 7, 2021
INVENTOR(S) : Anthony C. Perez et al.

It is certified that error appears in the above-identified patent and that said Letters Patent is hereby corrected as shown below:

In the Claims

Column 8, Line 17 (Claim 1, Line 8) delete "arid" and insert --and--

Column 8, Line 60 (Claim 6, Lines 7-14) after the word "wall," delete "c) wherein the first and second casing members are mated to each other so that a first outer edge of the first surrounding side wall faces the second major face wall with at least a portion of the second surrounding side wall being in an overlapping, direct contact relationship with at least a portion of the first surrounding side wall to form a seam; and" and insert --c) wherein the first and second casing members are mated to each other so that a first outer edge of the first surrounding side wall faces the second major face wall with at least a portion of the second surrounding side wall being in an overlapping, direct contact relationship with at least a portion of the first surrounding side wall to form a seam; and-- so that "c)" and its text begins at Line 61

Column 9, Line 16 (Claim 8, Lines 8-12) delete "b) the second electrode active material is an anode active material selected from the group of tantalum, aluminum, titanium, niobium, zirconium, hafnium, tungsten, molybdenum, vanadium, silicon, germanium, and mixtures thereof." and insert --b) the second electrode active material is an anode active material selected from the group of tantalum, aluminum, titanium, niobium, zirconium, hafnium, tungsten, molybdenum, vanadium, silicon, germanium, and mixtures thereof-- so that "b)" and its respective text, aligns with the line indent of a) of Claim 8

Column 9, Line 57 (Claim 14, Line 13) delete "arid" and insert --and--

Column 10, Line 3 (Claim 14, Line 19) delete "insulatin" and insert --insulating--

Signed and Sealed this
Seventeenth Day of January, 2023

Katherine Kelly Vidal
*Director of the United States Patent and Trademark Office*